(12) United States Patent
Constantine et al.

(10) Patent No.: US 9,561,173 B2
(45) Date of Patent: Feb. 7, 2017

(54) COSMETIC COMPOSITION AND METHOD FOR MAKING THE SAME

(71) Applicant: Cosmetic Warriors Limited, Poole, Dorset (GB)

(72) Inventors: Margaret Joan Constantine, Poole (GB); Mark Constantine, Poole (GB); Helen Elizabeth Ambrosen, Wimborne (GB)

(73) Assignee: Cosmetic Warriors Limited, Poole, Dorset (GB)

( * ) Notice: Subject to any disclaimer, the term of this patent is extended or adjusted under 35 U.S.C. 154(b) by 0 days.

(21) Appl. No.: 14/440,250

(22) PCT Filed: Oct. 23, 2013

(86) PCT No.: PCT/GB2013/052760
§ 371 (c)(1),
(2) Date: May 1, 2015

(87) PCT Pub. No.: WO2014/068282
PCT Pub. Date: May 8, 2014

(65) Prior Publication Data
US 2015/0297501 A1    Oct. 22, 2015

(30) Foreign Application Priority Data
Nov. 1, 2012 (GB) .................. 1219657.2

(51) Int. Cl.
*A61K 8/92* (2006.01)
*A61K 8/02* (2006.01)
*A61Q 19/00* (2006.01)

(52) U.S. Cl.
CPC ............ *A61K 8/922* (2013.01); *A61K 8/0233* (2013.01); *A61Q 19/00* (2013.01); *A61K 2800/56* (2013.01); *A61K 2800/5922* (2013.01)

(58) Field of Classification Search
CPC ............... A61K 8/922; A61K 8/0233; A61K 2800/5922; A61K 2800/56; A61Q 19/00
See application file for complete search history.

(56) References Cited

U.S. PATENT DOCUMENTS

| | | | |
|---|---|---|---|
| 6,358,498 B1 * | 3/2002 | Yu | A61K 8/02 424/401 |
| 2005/0042276 A1 * | 2/2005 | Inchley | A61K 9/4816 424/452 |
| 2006/0292193 A1 | 12/2006 | Lee et al. | |

FOREIGN PATENT DOCUMENTS

| | | |
|---|---|---|
| EP | 1078625 | 2/2001 |
| FR | 2794614 | 12/2000 |
| KR | 10-1133098 | 4/2012 |
| WO | WO 2007/002431 | 1/2007 |
| WO | WO 2012/175970 | 12/2012 |

OTHER PUBLICATIONS

International Search report and Written Opinion for International Application No. PCT/GB2013/052760 mailed Nov. 11, 2014 (10 pages).

* cited by examiner

*Primary Examiner* — Aradhana Sasan
(74) *Attorney, Agent, or Firm* — Merchant & Gould P.C.

(57) ABSTRACT

A solid cosmetic composition includes (i) an outer layer having (a) a hard vegetable butter in an amount of 10 to 45 wt. % based on the outer layer, and (b) a soft vegetable butter in an amount of 55 to 80 wt. % based on the outer layer. The composition also includes an (ii) inner core which is (a) a soft vegetable butter composition; (b) a fondant; or (c) a liquid cosmetic.

27 Claims, No Drawings

COSMETIC COMPOSITION AND METHOD FOR MAKING THE SAME

This application is a National Stage Application of PCT/GB2013/052760, filed 23 Oct. 2013, which claims benefit of Serial No. 1219657.2, filed 1 Nov. 2012 in Great Britain and which applications are incorporated herein by reference. To the extent appropriate, a claim of priority is made to each of the above disclosed applications.

FIELD OF THE INVENTION

The present invention relates to a solid cosmetic product, a process for producing said product, and a product prepared by the method.

BACKGROUND TO THE INVENTION

The present invention relates to products particularly those for use in contact with the human body.

A cosmetic product which has been increasingly popular is massage bars. These products contain a solidified oil or fat moulded into a product which may be held easily in the hand. Alternatively a larger sized product may be made from which a small piece may be broken and then used. In use, the massage bar is applied to the skin of the recipient either as a complete bar or by breaking off a small piece of product which is then applied to the skin. These solid products are both popular for home use and for application by a professional masseur.

Products are known where some or all of the massage bar product is formed from fats having a relatively high solid fat content. If correctly manufactured, these fats which are firm and solid at room temperature will melt on contact with skin. However, such melting may require prolonged contact with skin. During this period of prolonged contact, the user being massaged is subject to the unpleasant feeling of hard fat in a solid form being applied to the skin.

In view of the above disadvantages in the use of hard massage bars, many users find it desirable to buy massage bars which melt easily and which are immediately soft to the touch and on the skin. This could of course be provided with by formulation of a massage bar containing a high proportion of soft fats with relatively low melting points. However such formulations would be difficult to deliver without the use of packaging. Packaging is to be avoided for reasons of cost but most importantly for the protection of the environment.

The present invention seeks to provide a solid cosmetic product which may be used as a massage bar and which allows for immediate contact with the skin without the user being massaged with hard solid fat which takes a significant period to melt when contacted with the skin.

SUMMARY OF THE INVENTION

In a first aspect, there is provided a solid cosmetic composition comprising
(i) an outer layer comprising
(a) a hard vegetable butter in an amount of 10 to 45 wt. % based on the outer layer, and
(b) a soft vegetable butter in an amount of 55 to 80 wt. % based on the outer layer;
and
(ii) an inner core which is
(a) a soft vegetable butter composition;
(b) a fondant; or
(c) a liquid cosmetic.

In a second aspect, there is provided a process for the production of a solid cosmetic composition comprising an outer layer and an inner core, wherein the outer layer and the inner core are distinct from each other and the outer layer envelops the inner core, the process comprising the steps of:
i) preparing an outer layer, wherein outer layer composition comprises
(a) a hard vegetable butter in an amount of 10 to 45 wt. % based on the outer layer, and
(b) a soft vegetable butter in an amount of 55 to 80 wt. % based on the outer layer;
(ii) preparing an inner core which is
(a) a soft vegetable butter composition;
(b) a fondant; or
(c) a liquid cosmetic
iii) enveloping the inner core with the outer layer.

In a third aspect, there is provided a product obtained or obtainable by a process as described herein.

In a fourth aspect, there is provided a cosmetic method comprising contacting the skin of a user with a solid cosmetic composition as described herein.

For ease of reference, these and further aspects of the present invention are now discussed under appropriate section headings. However, the teachings under each section are not necessarily limited to each particular section.

ADVANTAGES

If we have identified that by providing a solid cosmetic composition as described herein, a composition is prepared which holds its form and does not may be readily melt prior to use. By virtue of this property, it is possible to sell the product without unnecessary packaging. The solid cosmetic composition of the present invention may also be applied to skin and the selected combination of vegetable butters allow for the composition to readily melt on application to the skin. Thus by this selection of vegetable butters, on application to the skin the user is not subjected to the unpleasant feeling of a hard and as yet and melted butter being applied. The high proportion of "soft" butters contained in the first vegetable butter composition means that the cosmetic composition may be applied in a number of manners. The solid cosmetic composition may be contacted directly with the skin. The user alternatively may squeeze the entire product such that the first vegetable butter composition and the inner core are intermixed prior to use. The inner core may contain a selection of softer materials or may contain fragrance or other desirable materials. Thus by this squeezing and mixing of the outer layer and the inner core a desirable sensory effect is provided. In yet a further alternative the solid cosmetic composition may be broken into parts by the user. The correct amount of product may be selected by the user, for example to apply a single massage treatment, and the remainder of the product may be retained.

DETAILED DESCRIPTION

Composition

As discussed herein, in one aspect of the present invention, there is provided a solid cosmetic composition comprising
(i) an outer layer comprising
(a) a hard vegetable butter in an amount of 10 to 45 wt. % based on the outer layer, and (b) a soft vegetable butter in an amount of 55 to 80 wt. % based on the outer layer;
and
(ii) an inner core which is
(a) a soft vegetable butter composition;
(b) a fondant; or
(c) a liquid cosmetic.

It will be understood by one skilled in the art that the nature of a cosmetic product means that the product is not edible. Thus in a further aspect the present invention provides a non-edible solid cosmetic composition comprising
(i) an outer layer comprising
(a) a hard vegetable butter in an amount of 10 to 45 wt. % based on the outer layer, and
(b) a soft vegetable butter in an amount of 55 to 80 wt. % based on the outer layer;
and
(ii) an inner core which is
(a) a soft vegetable butter composition;
(b) a fondant; or
(c) a liquid cosmetic.

The solid products of the present invention are compositions which can substantially sustain their physical shape when unsupported by external means, e.g. packaging etc. Thus, they are considered to be solid, solid like, in solid form or in solid-like form at room temperature. For the avoidance of doubt the solid product must remain substantially solid at up to 30° C.

By solid-like, it is understood that some materials are considered on a day to day basis to be solid, yet over an extremely long period of time, may alter in shape, e.g. amorphous materials such as glass etc. However, they are considered to be solid-like as, for the purpose they fulfil, they are solid.

Due to the solid form of the compositions of the present invention, external packaging is not required to maintain the shape of the composition.

The vegetable butters used in the present invention are triglycerides which is found to be solid (including solid like, discussed above) at normal usage temperatures. For the avoidance of doubt the vegetable butter is a triglyceride which remains substantially solid at up to 30° C. It will be appreciated however that it is not a requirement that the vegetable butter have a solid fat content of 100% at normal usage temperatures. In a preferred aspect the solid fat has a solid fat content of at least 70%, preferably at least 80%, preferably at least 90%, preferably at least 95%, preferably at least 98%, preferably at least 99% at 25° C.

The present invention provides a cosmetic product which is solid. The vegetable butters incorporated into the solid product are typically used as agents in massage. However the solid cosmetic product of the present invention may be used in any manner in which the end user sees fit. For example, the cosmetic product may be used in one or more of the following applications: tooth preparations, lip balms, solid bath salts, moisturizers, skincare, body lotions, shampoos, solid conditioners, hair dressings, face masks, bath melts, bath oils, shower gels, shower jellies, solid fragrance, solid henna hair dyes, shaving preparations, deodorants and bubble baths. However, in a preferred aspect the solid cosmetic composition of the present invention is a massage bar.

The composition of the present invention is typically made by moulding of the product. In a typical process, the outer layer is formed and placed in a mould. This composition is allowed to solidify to provide a mould shape formed from the outer layer. Into this solidified outer layer is placed on the inner core. If complete enclosure or envelopment of the inner core is required, a further amount of this outer layer is applied to complete the encasement of the inner core.

In one preferred aspect the outer layer entirely envelops the inner core.

The term vegetable butter is understood by one skilled in the art and means a triglyceride obtainable from vegetable source which has the consistency of a butter.

Outer Layer

As discussed herein, the outer layer comprises
(a) a hard vegetable butter in an amount of 10 to 45 wt. % based on the outer layer, and
(b) a soft vegetable butter in an amount of 55 to 80 wt. % based on the outer layer.

In one aspect the outer layer is a first vegetable butter composition wherein the first vegetable butter composition comprises
(a) one or more high saturated vegetable butters, wherein the one or more high saturated vegetable butters are selected from vegetable butters having greater than 60 wt % saturated fatty acids based on the total fatty acids of the high saturated vegetable butter,
wherein the total amount of high saturated vegetable butters is 10 to 45 wt. % based on the first vegetable butter composition, and
(b) one or more low saturated vegetable butters, wherein the one or more low saturated vegetable butters are selected from vegetable butters having less than 60 wt % saturated fatty acids based on the total fatty acids of the low saturated vegetable butter,
wherein the total amount of low saturated vegetable butters is 55 to 80 wt. % based on the first vegetable butter composition.

The term vegetable butter is understood by one skilled in the art and means a triglyceride obtainable from vegetable source which has the consistency of a butter.

The one or more hard vegetable butters (also known as and referred to as high saturated vegetable butters) is preferably selected from Cocoa butter, Illipe butter, Murumuru butter, Kokum butter and mixtures thereof. In highly preferred aspect, the one or more hard vegetable butters is Cocoa butter.

The one or the one or more soft vegetable butters (also known as and referred to as low saturated vegetable butters) is preferably selected from Aloe butter, Avocado butter, Cupuacu butter, Macadamia Nut butter, Mango butter, Olive butter, Shea butter, Coconut butter, Pumpkin Seed butter, Peanut butter, And Almond butter, Coffee Bean butter, Refined butter, Hemp Seed butter, Mochacchino butter, Pistachio Nut butter, Shealoe butter and mixtures thereof. In a highly preferred aspect, the one or more soft vegetable butters is Shea butter.

In a preferred aspect, the outer layer comprises (a) the one or more hard vegetable butters in an amount of 10 to 45 wt. % based on the outer layer, and (b) the one or more soft vegetable butters in an amount of 55 to 80 wt. % based on the outer layer. In a preferred aspect, the outer layer comprises (a) the one or more hard vegetable butters in an amount of 10 to 35 wt % based on the outer layer, and (b) the one or more soft vegetable butters in an amount of 60 to 80 wt. % based on the outer layer. In a preferred aspect, the outer layer comprises (a) the one or more hard vegetable butters in an amount of 10 to 30 wt. % based on the outer layer, and (b) the one or more soft vegetable butters in an amount of 60 to 80 wt. % based on the outer layer. In a preferred aspect, the outer layer comprises (a) the one or more hard vegetable butters, in an amount of 15 to 35 wt. % based on the outer layer, and (b) the one or more soft vegetable butters in an amount of 65 to 75 wt. % based on the outer layer. In a preferred aspect, the outer layer comprises (a) the one or more hard vegetable butters, in an amount of 15 to 25 wt. % based on the outer layer, and (b) the one or more soft vegetable butters in an amount of 65 to 75 wt. % based on the outer layer Thus in one preferred aspect the outer layer comprises (a) a vegetable butter selected from Cocoa butter, Illipe butter, Murumuru butter, Kokum butter and mixtures thereof, in an amount of 15 to 25 wt. % based on the outer layer, and (b) a vegetable butter selected from Aloe butter, Avocado butter, Cupuacu butter, Macadamia Nut butter, Mango butter, Olive butter, Shea butter, Coconut butter, Pumpkin Seed butter, Peanut butter, And Almond butter, Coffee Bean butter, Refined butter, Hemp Seed butter, Mochacchino butter, Pistachio Nut butter, Shealoe butter and mixtures thereof, in an amount of 65 to 75 wt. % based on the outer layer In one preferred aspect the outer layer comprises (a) Cocoa butter in an amount of 10 to 45 wt. % based on the outer layer, and (b) Shea butter in an amount of 55 to 80 wt. % based on the outer layer. In one preferred aspect the outer layer comprises (a) Cocoa butter in an amount of 10 to 35 wt. % based on the outer layer, and (b) Shea butter in an amount of 55 to 80 wt. % based on the outer layer. In one preferred aspect the outer layer comprises (a) Cocoa butter in an amount of 10 to 30 wt. % based on the outer layer, and (b) Shea butter in an amount of 55 to 80 wt. % based on the outer layer. In one preferred aspect the outer layer comprises (a) Cocoa butter in an amount of 10 to 35 wt. % based on the outer layer, and (b) Shea butter in an amount of 60 to 80 wt. % based on the outer layer. In one preferred aspect the outer layer comprises (a) Cocoa butter in an amount of 10 to 30 wt. % based on the outer layer, and (b) Shea butter in an amount of 60 to 80 wt. % based on the outer layer. In a more preferred aspect, the outer layer comprises (a) Cocoa butter in an amount of 15 to 35 wt. % based on the outer layer, and (b) Shea butter in an amount of 65 to 75 wt. % based on the outer layer. In a more preferred aspect, the outer layer comprises (a) Cocoa butter in an amount of 15 to 25 wt. % based on the outer layer, and (b) Shea butter in an amount of 65 to 75 wt. % based on the outer layer.

The essential components of the outer layer are defined herein. However the composition may contain further additional components. For example, the outer layer may contain one or more additional vegetable butter is not specified herein.

In one aspect, the outer layer further comprises an oil, such as a vegetable, nut or plant oil. Preferably the outer layer comprises the oil in an amount of 1 to 10 wt. % based on the outer layer. Thus in a preferred aspect, the present invention provides a solid cosmetic composition comprising
(i) an outer layer comprising
  (a) a hard vegetable butter in an amount of 10 to 45 wt. % based on the outer layer, and
  (b) a soft vegetable butter in an amount of 55 to 80 wt. % based on the outer layer;
  (c) an oil selected from vegetable oils, nut oils and plant oils, wherein the oil is present in an amount of 1 to 10 wt. % based on the outer layer,
and
(ii) an inner core which is
  (a) a soft vegetable butter composition;
  (b) a fondant; or
  (c) a liquid cosmetic.

Inner Core

As discussed herein, the inner core selected from
(a) a soft vegetable butter composition;
(b) a fondant; or
(c) a liquid cosmetic.

In one aspect the inner core may be a cosmetic composition selected from
(a) a second vegetable butter composition comprising one or more vegetable butters, wherein the one or more vegetable butters contains vegetable butters having greater than 60 wt % saturated fatty acids based on the total fatty acids of the vegetable butter in an amount of less 10 wt. % based on the second vegetable butter composition;
(b) a cosmetic comprising a syrup and glycerine; and
(c) a liquid cosmetic.

In one aspect the inner core is a soft vegetable butter. In one aspect the inner core is a cosmetic comprising a syrup. and glycerine. In one aspect the inner core is a liquid cosmetic.

Preferably the liquid cosmetic is selected from plant oils, nuts oils and mixtures thereof. In one aspect the liquid oil is a plant oil. In one aspect the liquid oil is a nut oil.

In one preferred aspect the soft vegetable butter composition comprises one or more vegetable butters, wherein the one or more vegetable butters contain
(i) hard vegetable butters in an amount of less 10 wt. % based on the soft vegetable butter; and
(ii) one or more soft vegetable butters, wherein the one or more soft vegetable butters in an amount of 20 to 60 wt. % based on the soft vegetable butter composition Preferably the one or more soft vegetable butters of the second vegetable butter composition is selected from Aloe butter, Avocado butter, Cupuacu butter, Macadamia Nut butter, Mango butter, Olive butter, Shea butter, Coconut butter, Pumpkin Seed butter, Peanut butter, And Almond butter, Coffee Bean butter, Refined butter, Hemp Seed butter, Mochacchino butter, Pistachio Nut butter, Shealoe butter and mixtures thereof.

In one preferred aspect the vegetable butter of the soft vegetable butter composition comprises one or more vegetable butters, wherein the one or more vegetable butters contain
(i) hard vegetable butters in an amount of less 10 wt. % based on the soft vegetable butter composition; and
(ii) one or more soft vegetable butters in an amount of 20 to 60 wt. % based on the second vegetable butter composition, wherein the one or more soft vegetable butters are selected from Aloe butter, Avocado butter, Cupuacu butter, Macadamia Nut butter, Mango butter, Olive butter, Shea butter, Coconut butter, Pumpkin Seed butter, Peanut butter, And Almond butter, Coffee Bean butter, Refined butter, Hemp Seed butter, Mochacchino butter, Pistachio Nut butter, Shealoe butter and mixtures thereof.

In one preferred aspect the one or more soft vegetable butters is present in an amount of 20 to 60 wt. % based on the soft vegetable butter composition, such as in an amount of 25 to 55 wt. % based on the soft vegetable butter composition, such as in an amount of 30 to 50 wt. % based on the soft vegetable butter composition, such as in an amount of 35 to 45 wt. % based on the soft vegetable butter composition.

In a preferred aspect the soft vegetable butter composition further comprises (b) an oil, such as a vegetable, nut or plant oil. Preferably the soft vegetable butter composition comprises the oil in an amount of 10 to 50 wt. % based on the soft vegetable butter composition. Preferably the soft vegetable butter composition comprises the oil in an amount of 15 to 45 wt. % based on the soft vegetable butter composition. Preferably the soft vegetable butter composition comprises the oil in an amount of 20 to 40 wt. % based on the soft vegetable butter composition. Preferably the soft vegetable butter composition comprises the oil in an amount of 25 to 35 wt. % based on the soft vegetable butter composition.

The inner core may be a fondant. Cosmetics comprising a syrup and glycerine are typically known in the art as a cosmetic fondant. Fondants are a blend of syrups (typically in a range of 1%-30 wt %, with advantageous results being achieved at approximately 20 wt %), oils/butters (typically in a range of 20%-90 wt %, with advantageous results being achieved at approximately 60 wt. %) and glycerine (typically in a range of 1%-20%, with advantageous results being achieved at approximately 12 wt. %). Syrups are a blend of thick, viscous liquid consisting primarily of a solution of sugar in water, containing a large amount of dissolved sugars but showing little tendency to deposit crystals. Cosmetic fondants may also comprise fruit puree, vegetable puree or mixtures thereof. In one aspect the fondant is selected from (a) mixtures of syrup and glycerine, (b) fruit puree, (c) vegetable puree and (d) mixtures thereof.

The essential components of the inner core are defined herein. However the composition may contain further additional components. For example, the soft vegetable butter composition may contain one or more additional vegetable butters not specified herein.

Outer Layer & Inner Core

When cocoa butter is used in the present invention, the cocoa butter may optionally be combined with cocoa solids. When the cocoa butter is combined with cocoa solids it may give the appearance of a chocolate type product.

The outer and inner layer may be present in suitable relevant amounts to provide the desired properties for the product. In one aspect, the outer layer is 60-85 wt. % and the inner core is 15 to 40 wt %, based on the combined weight of the inner core and outer layer.

The combined amount of the vegetable butters may be present in any amount to provide the desired physical characteristics of the solid cosmetic product. Preferably vegetable butter is present in the solid cosmetic product in an amount of from about 10% to about 99% by weight of the total composition. Preferably vegetable butter is present in the solid cosmetic product in an amount of from about 20% to about 99% by weight of the total composition. Preferably vegetable butter is present in the solid cosmetic product in an amount of from about 30% to about 99% by weight of the total composition. Preferably vegetable butter is present in the solid cosmetic product in an amount of from about 40% to about 99% by weight of the total composition. Preferably vegetable butter is present in the solid cosmetic product in an amount of from about 50% to about 99% by weight of the total composition. Preferably vegetable butter is present in the solid cosmetic product in an amount of from about 60% to about 99% by weight of the total composition. Preferably vegetable butter is present in the solid cosmetic product in an amount of from about 70% to about 99% by weight of the total composition.

The combined amount of the outer layer and the inner core in any amount to provide the desired physical characteristics of the solid cosmetic product. Preferably the combined amount of the outer layer and the inner core is from about 10% to about 100% by weight of the total composition. Preferably the combined amount of the outer layer and the inner core is from about 20% to about 100% by weight of the total composition. Preferably the combined amount of the outer layer and the inner core is from about 30% to about 100% by weight of the total composition. Preferably the combined amount of the outer layer and the inner core is from about 40% to about 100% by weight of the total composition. Preferably the combined amount of the outer layer and the inner core is from about 50% to about 100% by weight of the total composition. Preferably the combined amount of the outer layer and the inner core is from about 60% to about 100% by weight of the total composition. Preferably the combined amount of the outer layer and the inner core is from about 70% to about 100% by weight of the total composition. Preferably the combined amount of the outer layer and the inner core is from about 80% to about 100% by weight of the total composition. Preferably the combined amount of the outer layer and the inner core is from about 85% to about 100% by weight of the total composition. Preferably the combined amount of the outer layer and the inner core is from about 90% to about 100% by weight of the total composition. Preferably the combined amount of the outer layer and the inner core is from about 95% to about 100% by weight of the total composition. Preferably the combined amount of the outer layer and the inner core is 100% by weight of the total composition.

Additional Components

The solid product of the present invention may also comprise one or more cosmetically acceptable additives. The person skilled in the art is aware of a range of cosmetically acceptable additives which are suitable for incorporation into such compositions. For example, binders, fillers, opacifiers, perfumes, fragrances, decorative items and mixtures thereof.

It is particularly preferred that the composition of the present invention further comprises a fragrance. Preferably the fragrance is selected from essential oils. Preferably the fragrance, and more preferably the essential oil, is present in an amount of from about 0.5% to about 10% by weight of the total composition. More preferred amounts are from about 1% to about 8% by weight of the total composition, such as from about 2% to about 8% by weight of the total composition, such as from about 3% to about 7% by weight of the total composition, such as from about 4% to about 6% by weight of the total composition, such as approximately 5% by weight of the total composition.

In one aspect the outer layer comprises a fragrance in an amount of 1 to 10 wt. % based on the outer layer, and wherein the inner core comprises a fragrance in an amount of 1 to 10 wt. % based on the inner core.

Fruit and herb extracts and juices, vegetable oils and essential oils are all compatible with the composition. Colours, both naturally derived and synthetic can be used to colour the product.

In one embodiment, the cosmetically acceptable additives are selected from the group consisting of essential oils, vitamins, fragrances, colourings, clays, decorative articles and mixtures thereof.

The essential oils may be selected based on the fragrance desired, skin type to be treated and other effects desired based on the well known properties of essential oils. The addition of essential oils, when taken in to the nose, are known to alter mood. For example, essential oils are known to create effects of drowsiness or stimulating the senses. Many well documented effects can be achieved by the use of essential oils.

In one embodiment, the one or more essential oils present in the solid product are selected from Tarragon, Lemon myrtle, Jasmin, Ylang ylang, Labdunum, Lemongrass, Rose otto, Grapefruit, Patchouli, Rosemary, Armois, Lemon, Neroli, Sweet violet, Lavender, Orange 50 fold, Vanilla, Peppermint, Benzoin, Hydrangia, *Litsea Cubeba*, Cardamon, Tonka, and Chamomile blue. In one embodiment, the one or more essential oils present in the solid product are selected from Tarragon, Lemon myrtle, Labdunum, and Lemon.

Vitamins, particularly B, C and E are very beneficial for the skin. Vitamin rich ingredients such as Wheatgerm oil can also be used to deliver vitamins on to the skin. In a one embodiment, the vitamins are selected from vitamin B, vitamin C, vitamin E and mixtures thereof. It will be appreciated by one skilled in the art that the vitamin may be provided from any suitable source. For example the vitamin(s) may be provided from a synthetic source or from incorporation into the solid product of a material, such as a natural material, that has a high vitamin content.

The ingredients in the present invention do not require cosmetic preservatives. The use of cosmetic preservatives can increase the potential to irritate the skin.

The decorative items which may be present in the solid product include items such as glitter, paper such as rice paper, sequins, dried or fresh flowers, herbs, vegetables, parts thereof or mixtures thereof. Other enhancing materials may also be incorporated Further preferred additive materials include vegetable oils, chocolate, herbs and spices, cosmetic colours (e.g. paprika, gardenia extract, D&C red no. 30), beans (e.g. aduki), fruit, fresh or dried (e.g. banana, avocado, mango, papaya, kiwi, raspberry, strawberry, blueberries, grapes, tomato, asparagus, or cucumber), honey, glycerin, cosmetic glitter, other vegetable butters (e.g. mango, avocado), clays (e.g. kaolin), starches (e.g. corn starch) and mixtures thereof.

The above ranges provide preferred amounts of each of the components. Each of these ranges may be taken alone or combined with one or more other component ranges to provide a preferred aspect of the invention.

Process

As discussed herein, the invention provides a process for the production of a solid composition as described herein; the process comprising the steps of:
i) preparing the outer layer and the inner core;
ii) enveloping the inner core with the outer layer.

The shape of the solid products of the present invention is not limited. It may be that the solid products are provided with a shape which would be aesthetically pleasing and/or which aids in the use of the product. For example, it may be that the solid product is produced in such a manner so that it solidifies in a shape which is ergonomically acceptable to the user. Therefore, in one embodiment of the process of the present invention, the mixture of step i) and/or step ii) is pressed into a mould, allowed to solidify, and then turned out to produce the solid product.

As described herein, the solid product may further comprise one or more cosmetically acceptable additives. In one embodiment, the process further comprises the step of combining with the mixture of step i) and/or step ii) one or more cosmetically acceptable additives as defined herein and/or the dispersant defined herein.

The present invention also provides a product obtained or obtainable by a process as described herein.

Method

In one aspect of the present invention, there is provided a method comprising contacting the skin of a user with the present product. The product may be self-applied by the user or applied by another individual

EXAMPLE

The invention will now be described with reference to the following non-limiting example.

A general methodology for preparing compositions in accordance with the present invention is as follows:
1. the vegetable butters of the outer layer are heated to a temperature of 50-70° C. to melt.
2. Cool the butter mix down to 22-32° C., then re-heat to 33-45° C.
3. Any additional components, such as decorative materials, fragrances and colourings.
4. The mixture is then poured into a mould and left to solidify at temperature of 4-20° C.
5. the components of the inner core are heated in the same manner as step 1
6. if appropriate, syrup and glycerine are added and the mixture brought a temperature of 30-50° C.
7. any additional components, such as decorative materials, fragrances and colourings are added
8. the inner core is added to the shell of the outer layer.
9. This is optionally sealed with further amount of outer layer
10. composition is allowed to cool to 4° C. to set A outer layer having the following composition was prepared.

|   | Formula % | Raw Material Type | Batch Size: 136.00 g |
|---|---|---|---|
| A | 20.00 | Cocoa butter | 27.200 g |
|   | 72.00 | Shea butter | 97.920 g |
|   | 3.00 | Castor oil | 4.080 g |
| B | 5.00 | Fragrance | 6.800 g |
|   | 100.00 |   | 136.0 g |

The product was prepared as follows:
1. Warm A to 68° C. to melt.
2. Cool the butter mix down to 30° C., then re-heat to 40° C.
3. Cool the butter mix down to 27° C., add B A soft vegetable butter composition having the following composition was prepared.

|   | Formula % | Raw Material Type | Batch Size: 64.00 g |
|---|---|---|---|
| A | 40.00 | Shea butter | 25.600 g |
|   | 29.85 | Castor oil | 19.104 g |
| B | 15.00 | Maple Syrup | 9.600 g |
|   | 10.00 | Glycerine | 6.400 g |
|   | 0.15 | Colour Agents | 0.096 g |
| C | 5.00 | Fragrance | 3.200 g |
|   | 100.00 |   | 64.0 g |

The product was prepared as follows:
1. Warm A to 68° C. to melt
2. Cool A to 45° C., then stir in B+C,
3. cool to 8° C. to set The inner and outer were combined as follows
1. Fill a moulds with 58% of the 136 g of outer layer that has been prepared.
2. Add an inner mould, then cool 8° C. to set. Keep back the remaining 42% of the 136 g of the outer layer and maintain at 25° C.
3. Once the shell has solidified, remove the inner mould and
4. add the 64 g of the second vegetable butter composition
5. cover with the remaining 32% of the 136 g of outer layer
6. Cool 8° C. to set It was found that the prepared samples could be handled without undue oiling of the outer layer. The samples were then squeezed to mix the outer and inner compositions. These were then applied in a massage, found to have a pleasing and smooth texture.

In further aspects the present invention provides the compositions, processes and methods described in the following numbered paragraphs:

All references herein to an outer layer, refer to, encompass and may be read to be equivalent to a first vegetable butter composition, wherein the first vegetable butter composition comprises (a) one or more high saturated vegetable butters, wherein the one or more high saturated vegetable butters are selected from vegetable butters having greater than 60 wt % saturated fatty acids based on the total fatty acids of the high saturated vegetable butter, wherein the total amount of high saturated vegetable butters is 10 to 45 wt. % based on the first vegetable butter composition, and (b) one or more low saturated vegetable butters, wherein the one or more low saturated vegetable butters are selected from vegetable butters having less than 60 wt % saturated fatty acids based on the total fatty acids of the low saturated vegetable butter, wherein the total amount of low saturated vegetable butters is 55 to 80 wt. % based on the first vegetable butter composition.

All references herein to an inner core, refer to, encompass and may be read to be equivalent to a cosmetic material, wherein the cosmetic material is selected from (a) a second vegetable butter composition comprising one or more vegetable butters, wherein the one or more vegetable butters contains vegetable butters having greater than 60 wt % saturated fatty acids based on the total fatty acids of the vegetable butter in an amount of less 10 wt. % based on the second vegetable butter composition;

(b) a cosmetic comprising a syrup and glycerine; and (c) a liquid cosmetic.

1. A solid cosmetic composition comprising
   (i) a first vegetable butter composition, wherein the first vegetable butter composition comprises
      (a) one or more high saturated vegetable butters, wherein the one or more high saturated vegetable butters are selected from vegetable butters having greater than 60 wt % saturated fatty acids based on the total fatty acids of the high saturated vegetable butter,
      wherein the total amount of high saturated vegetable butters is 10 to 45 wt. % based on the first vegetable butter composition, and
      (b) one or more low saturated vegetable butters, wherein the one or more low saturated vegetable butters are selected from vegetable butters having less than 60 wt % saturated fatty acids based on the total fatty acids of the low saturated vegetable butter,
      wherein the total amount of low saturated vegetable butters is 55 to 80 wt. % based on the first vegetable butter composition;
   and
   (ii) a cosmetic material selected from
      (a) a second vegetable butter composition comprising one or more vegetable butters, wherein the one or more vegetable butters contains vegetable butters having greater than 60 wt % saturated fatty acids based on the total fatty acids of the vegetable butter in an amount of less 10 wt. % based on the second vegetable butter composition;
      (b) a cosmetic comprising a syrup and glycerine; and
      (c) a liquid cosmetic
   wherein the first vegetable butter composition and the cosmetic material are distinct from each other and the first vegetable butter composition envelops the cosmetic material.

2. A solid cosmetic composition according to paragraph 1 wherein first vegetable butter composition entirely envelops the cosmetic material.

3. A solid cosmetic composition according to paragraph 1 or 2 wherein the first vegetable butter composition comprises
   (a) the one or more high saturated vegetable butters, in an amount of 15 to 35 wt. % based on the first vegetable butter composition, and
   (b) the one or more low saturated vegetable butters in an amount of 65 to 75 wt. % based on the first vegetable butter composition 4. A solid cosmetic composition according to any one of paragraphs 1 to 3, wherein the one or more high saturated vegetable butters is selected from Cocoa butter, Illipe butter, Murumuru butter, Kokum butter and mixtures thereof.

5. A solid cosmetic composition according to any one of paragraphs 1 to 4, wherein the one or more high saturated vegetable butters is Cocoa butter.

6. A solid cosmetic composition according to any one of paragraphs 1 to 5, wherein the one or the one or more low saturated vegetable butters is selected from Aloe butter, Avocado butter, Cupuacu butter, Macadamia Nut butter, Mango butter, Olive butter, Shea butter, Coconut butter, Pumpkin Seed butter, Peanut butter, And Almond butter, Coffee Bean butter, Refined butter, Hemp Seed butter, Mochacchino butter, Pistachio Nut butter, Shealoe butter and mixtures thereof.

7. A solid cosmetic composition according to any one of paragraphs 1 to 6, wherein the one or more low saturated vegetable butters is Shea butter.

8. A solid cosmetic composition according to any one of paragraphs 1 to 7 wherein the first vegetable butter composition comprises
   (a) Cocoa butter in an amount of 10 to 45 wt. % based on the first vegetable butter composition, and
   (b) Shea butter in an amount of 55 to 80 wt. % based on the first vegetable butter composition 9. A solid cosmetic composition according to any one of paragraphs 1 to 7 wherein the first vegetable butter composition comprises
   (a) Cocoa butter in an amount of 15 to 35 wt. % based on the first vegetable butter composition, and
   (b) Shea butter in an amount of 65 to 75 wt. % based on the first vegetable butter composition.

10. A solid cosmetic composition according to any one of paragraphs 1 to 9, wherein the first vegetable butter composition further comprises an oil, such as a vegetable, nut or plant oil.

11. A solid cosmetic composition according to paragraph 10 wherein the first vegetable butter composition comprises the oil in an amount of 1 to 10 wt. % based on the first vegetable butter composition.

12. A solid cosmetic composition according to any one of paragraphs 1 to 11, wherein the cosmetic material is the second vegetable butter composition.

13. A solid cosmetic composition according to paragraph 12, wherein the second vegetable butter composition comprises one or more vegetable butters,
wherein the one or more vegetable butters contain
(i) high saturated vegetable butters having greater than 60 wt % saturated fatty acids based on the total fatty acids of the vegetable butter in an amount of less 10 wt. % based on the second vegetable butter composition; and
(ii) one or more low saturated vegetable butters, wherein the one or more low saturated vegetable butters are selected from vegetable butters having less than 60 wt % saturated fatty acids based on the total fatty acids of the low saturated vegetable butter, wherein the total amount of low saturated vegetable butters is 20 to 60 wt. % based on the second vegetable butter composition 14. A solid cosmetic composition according to paragraph 13, wherein the one or more low saturated vegetable butters of the second vegetable butter composition is selected from Aloe butter, Avocado butter, Cupuacu butter, Macadamia Nut butter, Mango butter, Olive butter, Shea butter, Coconut butter, Pumpkin Seed butter, Peanut butter, And Almond butter, Coffee Bean butter, Refined butter, Hemp Seed butter, Mochacchino butter, Pistachio Nut butter, Shealoe butter and mixtures thereof.

15. A solid cosmetic composition according to paragraph 13 or 14, wherein the one or more low saturated vegetable butters of the second vegetable butter composition is selected from Aloe butter, Avocado butter, Cupuacu butter, Macadamia Nut butter, Mango butter, Olive butter, Shea butter, Coconut butter, Pumpkin Seed butter, Peanut butter, And Almond butter, Coffee Bean butter, Refined butter, Hemp Seed butter, Mochacchino butter, Pistachio Nut butter, Shealoe butter and mixtures thereof, in an amount of 20 to 60 wt. %.

16. A solid cosmetic composition according to any one of paragraphs 12 to 15 wherein the second vegetable butter composition further comprises an oil, such as a vegetable, nut or plant oil.

17. A solid cosmetic composition according to paragraph 16 wherein the second vegetable butter composition comprises the oil in an amount of 10 to 50 wt. % based on the second vegetable butter composition.

18. A solid cosmetic composition according to any one of paragraphs 1 to 11, wherein the cosmetic material is a cosmetic comprising a syrup and glycerine.

19. A solid cosmetic composition according to any one of paragraphs 1 to 18, wherein the first vegetable butter composition and/or the cosmetic material further comprises at least one additional component selected from binders, fillers, opacifiers, perfumes, fragrances, decorative items and mixtures thereof.

20. A solid cosmetic composition according to any one of paragraphs 1 to 19, wherein the first vegetable butter composition and/or the cosmetic material further comprises a fragrance.

21. A solid cosmetic composition according to paragraph 20, wherein the fragrance is selected from essential oils.

22. A solid cosmetic composition according to paragraph 20 or 21, wherein the first vegetable butter composition comprises a fragrance in an amount of 1 to 10 wt. % based on the first vegetable butter composition, and wherein the cosmetic material comprises a fragrance in an amount of 1 to 10 wt. % based on the cosmetic material.

23. A solid cosmetic composition according to any one of paragraphs 1 to 22 wherein the composition is a massage bar.

24. A process for the production of a solid cosmetic composition as defined in paragraphs 1 to 23 comprising the steps of:
i) preparing the first vegetable butter composition and the cosmetic material;
ii) enveloping the cosmetic material with the first vegetable butter composition.

25. A product obtained or obtainable by the process of paragraph 24.

26. A cosmetic method comprising contacting the skin of a user with a solid cosmetic composition as defined in paragraphs 1 to 23.

Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, biology or related fields are intended to be within the scope of the following claims.

The invention claimed is:

1. A solid cosmetic composition comprising:
(i) an outer layer comprising:
(a) a hard vegetable butter in an amount of 10 to 45 wt. % based on the outer layer, and
(b) a soft vegetable butter in an amount of 55 to 80 wt. % based on the outer layer; and
(ii) an inner core comprising:
(a) a soft vegetable butter composition;
(b) a fondant; or
(c) a liquid cosmetic,
wherein the hard vegetable butter is a high saturated vegetable butter having greater than 60 wt. % saturated fatty acids based on total fatty acid content of the high saturated vegetable butter,
wherein the soft vegetable butter is a low saturated vegetable butter having less than 60 wt. % saturated fatty acids based on total fatty acid content of the low saturated vegetable butter, and
wherein the soft vegetable butter composition comprises one or more vegetable butters comprising less than 10 wt. % of hard vegetable butter by weight of the soft vegetable butter composition.

2. A solid cosmetic composition according to claim 1 wherein the outer layer entirely covers the inner core.

3. A solid cosmetic composition according to claim 1, wherein the outer layer comprises
(a) the hard vegetable butter in an amount of 15 to 35 wt. %, and
(b) the soft vegetable butter in an amount of 65 to 75 wt. %.

4. A solid cosmetic composition according to claim 1, wherein the hard vegetable butter is selected from cocoa butter, illipe butter, murumuru butter, kokum butter, and mixtures thereof.

5. A solid cosmetic composition according to claim 1, wherein the hard vegetable butter is cocoa butter.

6. A solid cosmetic composition according to claim 1, wherein the soft vegetable butter is selected from aloe butter, avocado butter, cupuacu butter, macadamia nut butter, mango butter, olive butter, shea butter, coconut butter, pumpkin seed butter, peanut butter, almond butter, coffee bean butter, refined butter, hemp seed butter, mochacchino butter, pistachio nut butter, shealoe butter, and mixtures thereof.

7. A solid cosmetic composition according to claim 1, wherein the soft vegetable butter is shea butter.

8. A solid cosmetic composition according to claim 1, wherein the outer layer comprises:
   (a) cocoa butter in an amount of 10 to 45 wt. % based on the outer layer, and
   (b) shea butter in an amount of 55 to 80 wt. % based on the first vegetable butter composition.

9. A solid cosmetic composition according to claim 1, wherein the outer layer comprises:
   (a) cocoa butter in an amount of 15 to 35 wt. %, and
   (b) shea butter in an amount of 65 to 75 wt. %.

10. A solid cosmetic composition according to claim 1, wherein the outer layer further comprises vegetable oil, nut oil or plant oil.

11. A solid cosmetic composition according to claim 10 wherein the outer layer comprises the oil in an amount of 1 to 10 wt. % based on the outer layer.

12. A solid cosmetic composition according to claim 1, wherein the inner core is a soft vegetable butter composition.

13. A solid cosmetic composition according to claim 12, wherein the inner core comprises one or more vegetable butters, wherein the one or more vegetable butters contain:
   (i) hard vegetable butters in an amount of less 10 wt. % based on the inner core; and
   (ii) soft vegetable butters in an amount of 20 to 60 wt. %.

14. A solid cosmetic composition according to claim 13, wherein the soft vegetable butters are selected from aloe butter, avocado butter, cupuacu butter, macadamia nut butter, mango butter, olive butter, shea butter, coconut butter, pumpkin seed butter, peanut butter, almond butter, coffee bean butter, refined butter, hemp seed butter, mochacchino butter, pistachio nut butter, shealoe butter, and mixtures thereof.

15. A solid cosmetic composition according to claim 13, wherein the soft vegetable butter is selected from aloe butter, avocado butter, cupuacu butter, macadamia nut butter, mango butter, olive butter, shea butter, coconut butter, pumpkin seed butter, peanut butter, almond butter, coffee bean butter, refined butter, hemp seed butter, mochacchino butter, pistachio nut butter, shealoe butter, and mixtures thereof, in an amount of 20 to 60 wt. %.

16. A solid cosmetic composition according to claim 12, wherein the inner core further comprises vegetable oil, nut oil or plant oil.

17. A solid cosmetic composition according to claim 16 wherein the inner core comprises the oil in an amount of 10 to 50 wt. % based on the second vegetable butter composition.

18. A solid cosmetic composition according to claim 1, wherein the inner core is a fondant.

19. A solid cosmetic composition according to claim 1, wherein the outer layer or the inner core further comprises at least one additional component selected from binders, fillers, opacifiers, perfumes, fragrances, decorative items and mixtures thereof.

20. A solid cosmetic composition according to claim 1, wherein the outer layer and/or the inner core further comprises a fragrance.

21. A solid cosmetic composition according to claim 20, wherein the fragrance is selected from essential oils.

22. A solid cosmetic composition according to claim 20, wherein the outer layer comprises a fragrance in an amount of 1 to 10 wt. % based on the outer layer, and wherein the inner core comprises a fragrance in an amount of 1 to 10 wt. % based on the inner core.

23. A solid cosmetic composition according to claim 1, wherein the outer layer is 60-85 wt. % and the inner core is 15 to 40 wt %, based on the combined weight of the inner core and outer layer.

24. A solid cosmetic composition according to claim 1, wherein the composition is a massage bar.

25. A process for the production of a solid cosmetic composition as defined in claim 1, the process comprising the steps of:
   i) preparing the outer layer and the inner core;
   ii) enveloping the inner core with the outer layer.

26. A product obtained or obtainable by the process of claim 25.

27. A cosmetic method comprising contacting the skin of a user with a solid cosmetic composition as defined in claim 1.

* * * * *